United States Patent [19]

Wang

[11] Patent Number: 4,981,976

[45] Date of Patent: Jan. 1, 1991

[54] POLYCYANATO RESINS

[75] Inventor: Pen C. Wang, Houston, Tex.

[73] Assignee: Shell Oil Company, Houston, Tex.

[21] Appl. No.: 314,518

[22] Filed: Feb. 23, 1989

[51] Int. Cl.$^5$ ............................................. C07D 491/00
[52] U.S. Cl. ..................................... 548/410; 548/407; 548/408; 548/409; 546/15
[58] Field of Search .................. 546/15, 407, 408, 409, 546/410

Primary Examiner—Nicholas S. Rizzo
Assistant Examiner—C. L. Cseh

[57] ABSTRACT

Cyanatoaryl-substituted 1,6-diaza[4.4]spirodilactam having a cyanatoaryl-containing substituent on each spiro ring nitrogen atom self-cure upon application of heat to produce cured, crosslinked thermoset resins of high glass transition temperature.

18 Claims, No Drawings

POLYCYANATO RESINS

FIELD OF THE INVENTION

This invention relates to monomeric resin materials which cure upon application of heat to produce crosslinked products exhibiting high glass transition temperatures. More particularly, the invention relates to a novel class of cyanato derivatives of hydroxyaryl-substituted 1,6-diaza [4.4] spirodilactams having a hydroxyaryl-substituent located on each spiro ring nitrogen atom.

BACKGROUND OF THE INVENTION

The curing of monomeric materials to produce thermoset resins is well known in the art. In general, the polymerizable monomers have at least one and customarily more than one active group which serves as the reactive site for a curing or crosslinking reaction to produce the thermoset resins which are typically highly crosslinked. The curing or crosslinking of many if not most thermoset resins, for example the curing of epoxy resins, requires the use of a curing agent, whether catalytic or stoichiometric, to cause the crosslinking reaction to proceed at an acceptable rate. Certain other monomers cure in the absence of added curing agent but only upon the application of high intensity energy, e.g., UV light. Even in the presence of most curing agents the rate of curing is unduly slow and the addition of an accelerator is generally required to obtain sufficiently rapid curing.

There are some monomers in which the active sites are such that no added curing agent is required and the monomers cure upon application of heat. Such monomers are termed "self-curing". The self-curing of such monomers results in production of crosslinked resins having good properties of rigidity and strength. Certain of the self-curing monomers are cyclic in character and the cured products which result therefrom are typically characterized by relatively high glass transition temperatures which provide dimensional stability in applications where elevated temperatures are likely to be encountered. It would be of advantage to provide a novel class of self-curing polycyclic monomeric materials which cure on application of heat to provide cured, crosslinked products of high glass transition temperature.

SUMMARY OF THE INVENTION

The present invention provides a novel class of self-curing compounds comprising cyanato derivatives of a substituted 1,6-diaza [4.4] spirodilactam. More particularly, the invention relates to cyanatoaryl derivatives of such a spirodilactam wherein cyanatoaryl substituents are located on the spiro ring nitrogen atoms. The invention also provides cured products obtained from the substituted spirodilactams by application of heat.

DESCRIPTION OF THE INVENTION

The novel spirodilactam derivatives of the invention are cyanatoaryl-substituted 1,6-diaza [4.4] spirodilactams wherein a cyanatoaryl substituent is located on each of the spiro ring nitrogen atoms. Although a wide variety of substituted spirodilactams having a variety of additional substituents are contemplated by the invention, a preferred class of such spirodilactams comprises spirodilactam derivatives of up to 60 carbon atoms represented by the formula

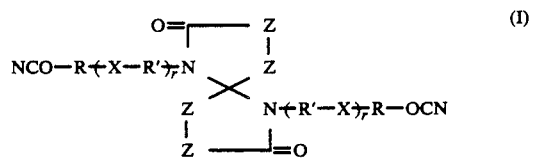

wherein R independently is aromatic of up to 15 carbon atoms and up to 2 aromatic rings, inclusive, R' independently is R or aliphatic of up to 10 carbon atoms inclusive, r independently is 0 or 1, X independently is a direct valence bond, alkylene of up to 8 carbon atoms inclusive, oxy, thio, sulfonyl, carbonyl, dioxyphenylene, 2,2-di(oxyphenyl)propane, di(oxyphenyl) sulfone or dioxydiphenylene, and Z independently is $>C(Z')_2$ in which Z' independently is hydrogen, lower alkyl, preferably methyl, halo, preferably the lower halogens fluoro or chloro, or aryl, preferably phenyl, or Z is such that two adjacent Z groups taken together form a ring system Z" of from 5 to 7 ring atoms up to two of which are heteroatoms selected from nitrogen, oxygen or sulfur with the remainder of the ring atoms being carbon atoms, there being up to 15 carbon atoms in each Z", two of which form a bridge between the carbon atoms connected by the adjacent Z groups. In the above formula I, R and R' are hydrocarbyl containing only atoms of carbon and hydrogen or are substituted hydrocarbyl containing additional atoms in the form of inert, monovalent carbon atom substituents such as halo, preferably the middle halogens chloro or bromo. A preferred class of substituted hydrocarbyl R or R' groups comprises halohydrocarbyl R or R' groups. R and R', when R' is aromatic, includes alkylaromatic and alkenylaromatic and when R' is aliphatic R' includes acyclic aliphatic, cycloaliphatic or arylaliphatic. A preferred R group or aromatic R' group has a single aromatic ring, i.e., is phenylene, particularly 1,4-phenylene or p-phenylene.

In the embodiment of the above formula I wherein the Z moieties are acyclic, i.e., not part of a fused cyclic ring system, Z is $>C(Z')_2$, illustrative cyanatoaryl-substituted spirodilactams are illustrated by 1,6-di(4-cyanatophenyl)-1,6-diazaspiro [4.4]nonane-2,7-dione, 1,6-di(4-cyanatophenyl)-1,6-diazaspiro[4.4]nonane-2,7-dione, 1,6-di(4-cyanato-3-chlorophenyl)-3,8-dimethyl-1,6-diazaspiro [4.4]nonane-2,7-dione, 1,6-di(3-cyanato-5-methylphenyl)-3,4,8,9-tetramethyl-1,6-diazaspiro[4.4]nonane-2,7-dione, 1,6-di(4-cyanato-3,5-dibromophenyl)-1,6-diazaspiro[4.4]nonane-2,7-dione, 1,6-di[4-(3-cyanatobenzoyl) phenyl]-1,6-diazaspiro[4.4]nonane-2,7-dione, 1,6-di(4-cyanatophenyl)-3,3,4,4,8,8,9,9-octamethyl-1,6-diazaspiro[4.4]-nonane-2,7-dione, 1,6-di[4-(4'-cyanatobiphenyl)]-1,6-diazaspiro[4.4]nonane-2,7-dione, 1,6-di[4-(4-cyanatophenylisopropyl)phenyl]-3,3-diphenyl-1,6-diazaspiro[4.4]nonane-2,7-dione and 1,6-di(4-cyanatophenyl)-3,4,8,9-tetrafluoro-1,6-diazaspiro[4.4] nonane-2,7-dione. In the embodiment of the spirodilactam derivatives of formula I wherein the adjacent Z moieties of each spiro ring form a cyclic, fused ring substituent, i.e., the adjacent Z groups are Z", illustrative spirodilactam derivatives include 1,6-di(4-cyanatophenyl)-3,4,8,9-dibenzo-1,6-diazaspiro[4.4]nonane-2,7-dione, and 1,6-di[4-(4-cyanato-3,5-dibromophenyloxy)phenyl]-3,4,8,9-di(pyrido)-1,6-diazaspiro[4.4]nonane-2,7-dione and 1,6-di(3-cyanatophenyl)-3,4,8,9-di(cyclopentano)-1,6-diazaspiro[4.4]nonane-2,7-dione. Also suitable are those substituted spirodilactams wherein one spiro ring has a fused ring substituent and one ring is free from fused ring substituents, e.g., 1,6-di[4-(4-cyanatophenylthio)phenyl]-3,4-benzo-8-methyl-1,6-diazaspiro[4.4]nonane-2,7-dione and 1,6-di[1-(4-cyanatonaphthyl)]-3,4-cyclo-4-hexeno- 1,6-diazaspiro[4.4]nonane-2,7-dione.

The cyanatoaryl-substituted spirodilactams of the above formula I wherein R and R' are aromatic and hydrocarbyl or halohydrocarbyl are preferred and further preference is given to such spirodilactams wherein r is 0 and R has a single aromatic ring. Within the spirodilactam ring portion of the molecule, spirodilactams free from fused ring substituents, i.e., Z is >C(Z')$_2$, are preferred as are those wherein both spiro rings incorporate a fused ring substituent. The compound 1,6-di(4-cyanatophenyl)-1,6-diazaspiro[4.4]nonane-2,7-dione is an especially preferred member of the former class whereas 1,6-di(4-cyanatophenyl)-3,4,8,9-dibenzo-1,6-diazaspiro[4.4]nonane-2,7-dione is an especially preferred member of the latter class.

The cyanatoaryl-substituted spirodilactams are produced by reaction of a cyanogen halide with the corresponding hydroxyaryl-substituted spirodilactam in the presence of a tertiary amine. In terms of the cyanatoaryl-substituted spirodilactams of formula I, the hydroxyaryl precursors are represented by the formula

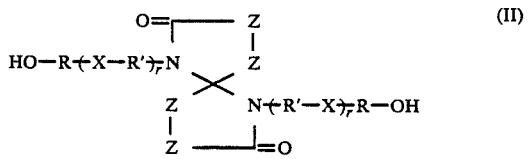

wherein R, R', X, r and Z have the previously stated meanings. The hydroxyaryl-substituted spirodilactams and methods for their production are described in more detail and are claimed in copending U.S. patent application Ser. No. 172,000, filed Mar. 23, 1988, Ser. No. 172,052, filed Mar. 23, 1988 and Ser. No. 245,618, filed Sept. 16, 1988. A special class of such spirodilactams having 2-alkenyl substituents on aromatic carbon atoms ortho to the hydroxyl group of the hydroxyaryl substituents is described and claimed in copending U.S. Pat. No. 4,886,863. Each of these applications is incorporated herein by reference.

The general procedure for the production of most of the spirodilactams of the above formula II is the reaction of a hydroxy-containing primary amino compound and a spirodilactam precursor selected from 4-oxo-heptanedioic acid compounds or 1,6-dioxo[4.4]spirodilactams. In terms of the hydroxyaryl-substituted spirodilactams of formula II, the hydroxy-containing primary amino compound is represented by the formula

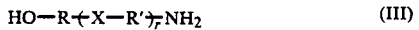

wherein R, R', r and X have the previously stated meanings. Also in terms of the spirodilactam of formula II, the 4-oxoheptandioic acid compounds are represented by the formula

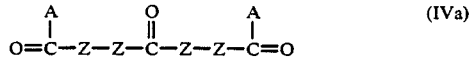

wherein Z has the previously stated meaning and A is hydroxy, alkoxy or halo, and the spirodilactones utilized as a spirodilactam precursor are represented by the formula

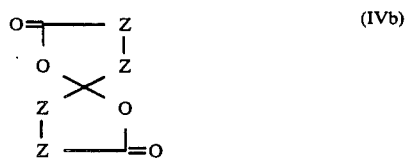

wherein Z has the previously stated meaning.

The hydroxy-containing primary amino compound and the spirodilactam precursor are typically contacted in a molar ratio of about 2:1 in the liquid phase in the presence of an inert reaction diluent capable of dissolving at least a portion of each reactant at reaction temperature. A preferred class of diluents comprises the N-alkylamides such as N,N-dimethylacetamide or N-methyl-2-pyrrolidone. Reaction conditions include a reaction temperature of from about 80° C. to about 200° C. and a reaction pressure sufficient to maintain the reaction mixture in the liquid phase. Such pressures are from about 1 atmosphere to about 20 atmospheres. Subsequent to reaction, the hydroxyaryl-substituted spirodilactam is recovered, if desired, by conventional methods such as extraction, solvent removal and precipitation. The isolation of the hydroxyaryl-substituted spirodilactam is not required, however, and the spirodilactam is suitably reacted further in situ without isolation. By way of specific illustration, p-aminophenol reacts with either 4-oxoheptanedioic acid or 1,6-dioxaspiro-[4.4]nonane-2,7-dione to produce 1,6-di(4-hydroxyphenyl)-1,6-diazaspiro-[4.4]nonane-2,7-dione and 4-amino-4'-hydroxybiphenyl reacts with either di(2-carboxyphenyl)ketone or 3,4,8,9-dibenzo-1,6-dioxaspiro[4.4]nonane-2,7-dione to produce 1,6-di[4-(4-hydroxybiphenyl)]-1,6-diazaspiro[4.4]nonane-2,7-dione. A somewhat special case exists when the hydroxyaryl-substituted spirodilactam has an alkenyl, e.g., allyl, substituent on an aromatic carbon atom ortho to the hydroxyl group of the hydroxyaryl substituent. Although such spirodilactams are produced by the above-described process, they are also easily produced by thermal Claisen Rearrangement of the alkenyl ether of the hydroxyaryl-substituted spirodilactam. The ethers are produced by reaction of the hydroxyaryl-substituted spirodilactams with an alkenyl halide such as allyl chloride. The ethers are claimed in more detail in copending U.S. patent application Ser. No. 245,433, filed Sept. 16, 1988 now U.S. Pat. No. 4,847,388.

The production of the cyanato derivatives of the invention is by reaction of the hydroxyaryl-substituted spirodilactam (formula I) with a cyanogen halide, preferably cyanogen chloride or cyanogen bromide, most preferably cyanogen bromide. The reaction of the cyanogen halide and the hydroxyaryl-substituted spirodilactam is conducted in a liquid phase at a reduced temperature in the presence of a tertiary amine employed to react with the hydrogen halide by-product and facilitate its removal from the reaction mixture through formation of a quaternary ammonium salt. The cyanogen halide and the spirodilactam react in a molar ratio of 2:1 and satisfactory resuts are obtained when the reactants are employed in subsstantially stoichiometric quantities or with a slight molar excess of the cyanogen halide. Molar ratios of cyanogen halide to substituted spirodilactam from about 8:1 to about 1:4 are useful, however.

The precise nature of the tertiary amine to be utilized is not critical although preferred tertiary amines react with the hydrogen halide produced during reaction to form a quaternary ammonium salt. The tertiary amine may be aromatic in character such as dimethylaniline or pyridine but good results are obtained with a trialkyl amine wherein each alkyl has up to 12 carbon atoms inclusive, but preferably a trialkylamine wherein each alkyl is lower alkyl of up to 4 carbon atoms inclusive. Trimethylamine is particularly useful in the process of producing the cyanato derivatives.

The reaction is conducted in the presence of a reaction diluent or mixture of diluents which is liquid at reaction temperature and is capable of dissolving at least a portion of each reactant. Such diluents include N-alkylamides such as N,N-dimethylformamide, N,N-dimethylacetamide or N-methyl-2-pyrrolidone, chlorinated hydrocarbons such as chloroform, methylene chloride or chlorobenzene, sulfur-containing diluents including dimethyl sulfoxide or sulfolane, ethers, e.g., acyclic ethers such as diethylene glycol diethyl ether or tetraethylene glycol dimethyl ether as well as cyclic ethers such as tetrahydrofuran or dioxane, or miscible mixtures thereof. The reaction is usually conducted by mixing the cyanogen halide and substituted spirodilactam in the reaction diluent, cooling the mixture to reaction temperature and slowly adding the tertiary amine. Reactant contact is maintained during reaction as by shaking or stirring. Reaction temperatures are generally from about −10° C. to about 15° C. and reaction pressures are sufficient to maintain the reaction mixture in the liquid phase, generally from about 0.8 atmosphere to about 10 atmospheres. Subsequent to reaction the cyanatoaryl-substituted spirodilactam of formula I is recovered by conventional methods including removal of the amine salt by-product as by filtration or decantation and separation of the spirodilactam derivative as by extraction or precipitation with a non-solvent.

The cyanatoaryl-substituted spirodilactams are generally solids with melting points typically in the 100° C. to 200° C. range. Although the cyanato materials react with conventional curing agents, the spirodilactam derivatives are self-curing and will cure or crosslink without the presence of added curing agent and/or accelerator by heating the cyanatoaryl-containing spirodilactam to a temperature above about 150° C. It is often desired to effect the curing in stages as by heating the cyanato derivative in a first stage to about 170°–180° C. to initiate the curing and completing the curing process at a higher temperature, e.g., 200°–250° C. The resulting cured products are thermosets with a highly crosslinked structure, good properties of strength and rigidity and a high glass transition temperature, on occasion in excess of 300° C. The cyanato-substituted spirodilactam products are processed by methods which are conventional for curing monomeric compounds upon application of heat. The resulting cured products find utility as structural and coating materials in the aerospace and electronic industries.

The invention is further illustrated by the following Illustrative Embodiments which should not be construed as limiting the invention.

ILLUSTRATIVE EMBODIMENT I

The compound 1,6-di(4-hydroxy-3-allylphenyl)-1,6-diazaspiro[4.4]nonane-2,7-dione is produced by reacting 1,6-di(4-hydroxyphenyl)-1,6-diazaspiro[4.4]nonane-2,7-dione with allyl chloride to produce the diallyl ether and subjecting the ether to a Claisen Rearrangement. This process is described in greater detail in copending U.S. Pat. No. 4,886,863.

A mixture of 60.44 g (0.14 mole) of this product and 33.7 g (0.32 mole) of cyanogen bromide was dissolved in 75 ml of N-methyl-2-pyrrolidone and 375 ml of chloroform in a 1 liter round bottom flask. The stirred solution was cooled to 0° C. and 32.2 g (0.32 mole) of triethylamine was added at a slow rate to maintain the temperature of the mixture at 5°–10° C. After the reaction was complete, the resulting triethylamine salt was removed by filtration and the filtrate was concentrated and poured dropwise into a mixture of ether and hexane. The resulting precipitate was recovered by filtration and dried in a vacuum oven at ambient temperature. The product had a melting point of 128°–131° C. and the nuclear magnetic resonance spectra were consistent with the structure of 1,6-di(4-cyanato-3-allylphenyl)-1,6-diazaspiro[4.4]nonane-2,7-dione.

ILLUSTRATIVE EMBODIMENT II

The cyanate resin of Illustrative Embodiment I was cured at 175° C. for 2 hours, 200° C. for 2 hours and 220° C. for 2 hours to give a cured material with a glass transition temperature in excess of 300° C.

What is claimed is:

1. A cyanatoaryl-substituted derivative of a hydroxyaryl-substituted 1,6-diaza [4.4] spirodilactam having up to 60 carbon atoms inclusive, said derivative having a cyanatoaryl-containing substituent on each of the 1- and 6- spiro ring nitrogen atoms.

2. The spirodilactam of claim 1 represented by the formula

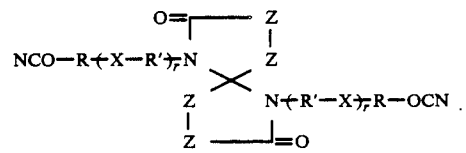

wherein R is aromatic of up to 15 carbon atoms and up to two aromatic rings, inclusive, R' is R or aliphatic of up to 10 carbon atoms, inclusive, X is a direct valence bond, alkylene of up to 8 carbon atoms inclusive, oxy, thio, sulfonyl, carbonyl, dioxyphenylene, 2,2-di(oxyphenyl)propane, di(oxyphenyl)sulfone or dioxydiphenylene, r is 0 or 1 and Z independently is >C(Z')$_2$ in which Z' is hydrogen, lower alkyl or lower halo, or Z is such that two adjacent Z groups taken together form a ring system Z" of from 5 to 7 ring atoms up to two of which are heteroatoms selected from nitrogen, oxygen or sulfur with the remainder of the ring atoms being carbon atoms, there being up to 15 carbon atoms in each Z", two of which form a bridge between the carbon atoms connected by the adjacent Z groups.

3. The spirodilactam of claim 2 wherein R' is R.

4. The spirodilactam of claim 3 wherein Z is >C(Z')$_2$.

5. The spirodilactam of claim 4 wherein r is 0.

6. The spirodilactam of claim 4 or 5 wherein Z' is hydrogen or methyl.

7. The spirodilactam of claim 6 wherein R is phenylene.

8. The spirodilactam of claim 7 wherein Z' is hydrogen.

9. The spirodilactam of claim 8 wherein R is p-phenylene.

10. The spirodilactam of claim 3 wherein adjacent Z groups are Z".

11. The spirodilactam of claim 10 wherein r is 0.

12. The spirodilactam of claim 11 wherein Z" is pyrido.

13. The spirodilactam of claim 10, or 11 wherein Z" is benzo.

14. The spirodilactam of claim 13 wherein R is phenylene.

15. The spirodilactam of claim 14 wherein R is p-phenylene.

16. A compound according to claim 6 wherein R is alkenylaromatic.

17. A compound according to claim 16 wherein R is 3-allyl-1,4-phenylene.

18. A compound according to claim 11 wherein R is alkenylaromatic.

* * * * *